(12) United States Patent
Heinrichs

(10) Patent No.: US 12,306,606 B2
(45) Date of Patent: May 20, 2025

(54) BIOREACTOR CLEANING INSTALLATION FOR BIOREACTORS IN RAIL VEHICLES

(71) Applicant: VOGELSANG GMBH & CO. KG, Essen (DE)

(72) Inventor: Martin Heinrichs, Essen (DE)

(73) Assignee: VOGELSANG GMBH & CO KG, Essen (DE)

(*) Notice: Subject to any disclaimer, the term of this patent is extended or adjusted under 35 U.S.C. 154(b) by 189 days.

(21) Appl. No.: 18/015,744

(22) PCT Filed: Jul. 13, 2021

(86) PCT No.: PCT/EP2021/069411
§ 371 (c)(1),
(2) Date: Jan. 12, 2023

(87) PCT Pub. No.: WO2022/013194
PCT Pub. Date: Jan. 20, 2022

(65) Prior Publication Data
US 2023/0332089 A1    Oct. 19, 2023

(30) Foreign Application Priority Data

Jul. 13, 2020 (DE) .................. 20 2020 104 037.5
Jul. 28, 2020 (DE) .................. 10 2020 119 924.4

(51) Int. Cl.
*G05B 19/40* (2006.01)
*B01D 29/11* (2006.01)
(Continued)

(52) U.S. Cl.
CPC ............ *G05B 19/406* (2013.01); *B01D 29/11* (2013.01); *B01D 29/66* (2013.01); *B08B 3/02* (2013.01);
(Continued)

(58) Field of Classification Search
CPC .................................................. G05B 19/406
See application file for complete search history.

(56) References Cited

FOREIGN PATENT DOCUMENTS

| CN | 110790452 | 2/2020 |
|---|---|---|
| DE | 140488 | 3/1980 |

(Continued)

OTHER PUBLICATIONS

Sudostbahn, "The quiet room is upgraded," Media release, St. Gallen, Switzerland (Jun. 26, 2017).

*Primary Examiner* — Jason Y Ko
(74) *Attorney, Agent, or Firm* — PRICE HENEVELD LLP

(57) ABSTRACT

A bioreactor cleaning system for cleaning a bioreactor in a rail vehicle, comprising a first suction connection, a second suction connection, a flushing connection, an acid tank, a collection tank for receiving liquid drawn out of the bioreactor, a fresh water connection, a pump with a first pump connection and a second pump connection, and a measuring unit for measuring liquid. By means of the pump liquid can be pumped from the first suction connection optionally into the measuring unit, into the collection tank or into the acid tank, aqueous acid solution can be pumped from the acid tank to the second suction connection and/or to the flushing connection; fresh water can be pumped from the fresh water connection selectively to the flushing connection or the measuring unit; and liquid can be pumped from the measuring unit either to the collection tank or to the second suction connection.

38 Claims, 5 Drawing Sheets

(51) Int. Cl.
    *B01D 29/66* (2006.01)
    *B08B 3/02* (2006.01)
    *B08B 3/08* (2006.01)
    *B08B 5/04* (2006.01)
    *B08B 13/00* (2006.01)
    *B61D 35/00* (2006.01)
    *C02F 3/00* (2023.01)
    *C12M 1/00* (2006.01)
    *C12M 1/36* (2006.01)
    *G05B 19/406* (2006.01)
    *C02F 103/00* (2006.01)

(52) U.S. Cl.
    CPC ............... *B08B 3/08* (2013.01); *B08B 5/04* (2013.01); *B08B 13/00* (2013.01); *B61D 35/007* (2013.01); *C02F 3/006* (2013.01); *C12M 29/00* (2013.01); *C12M 39/00* (2013.01); *C12M 41/48* (2013.01); *C12M 43/00* (2013.01); *C02F 2103/005* (2013.01); *C02F 2201/008* (2013.01); *C02F 2303/14* (2013.01); *C02F 2303/16* (2013.01); *G05B 2219/32234* (2013.01)

(56) References Cited

FOREIGN PATENT DOCUMENTS

| | | |
|---|---|---|
| DE | 19524960 | 1/1997 |
| DE | 102015222989 | 5/2017 |
| DE | 102016115393 | 12/2017 |
| DE | 202017101065 | 5/2018 |
| DE | 102017208852 | 11/2018 |
| EP | 1559775 | 8/2005 |
| EP | 2098280 | 9/2009 |
| EP | 2364893 | 9/2011 |
| EP | 2789683 | 10/2014 |
| EP | 3404090 | 11/2018 |
| WO | 03010097 | 2/2003 |
| WO | 2017207494 | 12/2017 |

BIOREACTOR CLEANING INSTALLATION FOR BIOREACTORS IN RAIL VEHICLES

CROSS-REFERENCE TO FOREIGN PRIORITY APPLICATION

The present application claims the benefit under 35 U.S.C. §§ 119(b), 119(e), 120, and/or 365(c) of PCT/EP2021/069411 filed Jul. 13, 2021, which claims priority to German Application No. DE 20 2020 104 037.5 filed Jul. 13, 2020, and to German Application No. DE 10 2020 119 924.4 filed Jul. 28, 2020.

FIELD OF THE INVENTION

The invention relates to a bioreactor cleaning system for cleaning a bioreactor, preferably a bioreactor in a rail vehicle, having a first suction connection for connecting to the bioreactor, a second suction connection for connecting to the bioreactor, via which a liquid can be suctioned out of a filter basket of the bioreactor, a flushing connection for supplying a liquid to a cleaning nozzle of the bioreactor, an acid tank for receiving an aqueous acid solution, a collection tank for receiving liquid extracted from the bioreactor, a freshwater connection for supplying fresh water to the bioreactor cleaning system, and a pump having a first pump connection and a second pump connection. In stationary systems, the collection tank may also be omitted and the liquid extracted from the bioreactor may be supplied directly to a sewer drain. The invention further relates to a method for operating such a bioreactor cleaning system, in particular for maintaining and/or cleaning a bioreactor, and to a computer program for controlling the bioreactor cleaning system.

BACKGROUND OF THE INVENTION

Conventional bioreactors have a solids tank with a filter basket into which wastewater with solid and liquid components is fed. The filter basket separates the solid from the liquid components. For this purpose, the filter basket has filter elements at the surrounding walls, such as the bottom and side walls, through which liquid elements can flow off and by means of which solid elements are collected. The solid elements separated from the liquid elements collect at the bottom inside the filter basket and form a filter cake. The liquid elements flow through the filter elements into the solids tank and from there into a liquid tank, which is in fluid communication with the solids tank.

It is known that the solid elements in the filter basket settle as a filter cake. First, a filter cake is formed starting at a bottom side of the filter basket and then at the sides of the filter basket. As a result, the water is inhibited by the filter cake from flowing into the solids tank. A filter cake with some permeability results in an efficient filtration process. However, an increasingly thick and impermeable filter cake can cause the filter basket to clog. This results in an inefficient filtering process, as the liquid hardly passes through the filter anymore. It is therefore necessary to clean the filter basket of solids at regular intervals to ensure adequate drainage of the water into the solids tank.

It is known to remove the filter cake to counteract this clogging. Often, the filter cake is removed as soon as the first effects of clogging appear. However, this has the disadvantage that inefficient filtration has already taken place. It is also known to check the amount of filter cake from time to time to determine if removal is necessary. However, this has the disadvantage that the check is carried out randomly, and the correct time, i.e., neither too early nor too late, for removal of the filter cake cannot be reliably determined in this way. In addition, it is not possible to reliably assess whether the filter cake is already so impermeable that it must be removed.

One problem with such cleaning processes, however, is that bioreactors are usually constructed as closed systems and it is therefore very difficult to determine the degree of contamination and the cause of insufficient filtration. Existing bioreactors, in particular, often do not have interfaces that can be used to read out the information required to determine the cause of a fault or the degree of contamination, or even data that is helpful for this purpose. This is particularly difficult if such a bioreactor is installed onboard a vehicle, such as a rail vehicle, in order to clean the wastewater that accumulates there. In such applications, maintenance and assurance of the bioreactor's function is often desired decentrally and without its removal, but at the same time, due to the necessary compactness, access to the bioreactor and to data describing its condition is not possible or only possible at great efforts.

In addition, there are problems in performing cleaning. Handling between different operators varies and so the cleaning result may depend on the skill of the particular operator.

It is therefore an object of the present invention to provide a bioreactor cleaning system of the above mentioned type, which is simple in design, not very prone to error, versatile in use and, as far as possible, allows a uniform and constantly good cleaning of a bioreactor.

SUMMARY OF THE INVENTION

The invention solves this problem in a bioreactor cleaning system of the type mentioned above with the features as claimed, namely, in particular, in that on the one hand a measuring unit for measuring liquid is provided, and wherein by means of the pump liquid can be pumped from the first suction connection optionally to the measuring unit, to the collection tank or to the acid tank, an aqueous acid solution can be pumped from the acid tank to the second suction connection and/or to the flushing connection, freshwater can be pumped from the freshwater connection optionally to the flushing connection or the measuring unit, and liquid can be pumped from the measuring unit optionally into the collecting tank or to the second suction connection. In stationary systems, the collection tank can also be omitted and the liquid extracted from the bioreactor can be fed directly to a sewer drain.

The invention is based on the realization that, on the one hand, the functionality of the bioreactor cleaning system as a whole can be improved and extended by clever interconnection of the individual elements and functional units of the bioreactor cleaning system and, on the other hand, that the measuring unit for measuring the liquid can be used to implement functions, such as, in particular, testing a permeability of the bioreactor, cleaning the bioreactor with a pressurized liquid, e.g., freshwater, and cleaning the bioreactor with a chemical, such as, in particular, an aqueous acid solution. The interconnection of the individual elements allows automated operation or largely automated operation from the provision of an aqueous acid solution to testing the permeability of the bioreactor.

The term liquid is understood in the present disclosure as a generic term for substances such as freshwater, aqueous acid solutions, acid, wastewater, and also viscous fluids, in particular, sludge, and the like. The term aqueous acid solution as used in the present disclosure means a liquid, which is a mixture of an acid and water.

The pump is preferably a rotary lobe pump, which is designed to pump from the first pump connection to the second pump connection, as well as vice versa from the second pump connection to the first pump connection. Other types of pumps are also preferred, such as peristaltic pumps or the like. Rotary lobe pumps have the advantage that even fluids loaded with solids can be pumped, while also providing a sufficient degree of tightness and high wear resistance.

The collection tank is preferably designed to be able to receive all kind of liquids. This applies to liquids extracted from the bioreactor, i.e., liquids that are already present in the bioreactor before the start of the cleaning process, as well as liquids that have been introduced into the bioreactor as a result of cleaning. For example, if mechanical cleaning of the bioreactor is carried out using a nozzle located in the bioreactor and freshwater under pressure, the liquid subsequently present in the bioreactor can be extracted and stored in the collection tank. The collection tank thus serves as an intermediate storage tank and the liquid present therein can be disposed of after completion of the cleaning process. Preferably, aqueous acid solution is stored in the acid tank. This aqueous acid solution is used to perform chemical cleaning of the bioreactor, such as, in particular, removal of lime. After chemical cleaning has been completed, the aqueous acid solution is again suctioned out of the bioreactor and, if it is still of sufficient quality to be used in a further cleaning process, can then be stored in the acid tank again. However, if the aqueous acid solution is to be disposed of, it can first be neutralized in the acid tank for neutralization purposes, or it can be added directly to the collection tank for subsequent disposal at a suitable location under appropriate conditions.

The individual connections of the bioreactor cleaning system are preferably equipped with appropriate couplings, such as camlock couplings or the like. Bioreactors provided in trains have standard connections to which the bioreactor cleaning system can be connected in accordance with the invention described herein.

In a first preferred embodiment, the bioreactor cleaning system comprises an electronic control unit, at least for controlling the pump, wherein the electronic control unit comprises a memory and a processor and is adapted to receive at least one first parameter from at least one sensor of the bioreactor cleaning system and/or at least one second parameter from a user via the human-machine interface, and wherein the electronic control unit controls the pump based on the first and second parameters. Furthermore, the electronic control unit may be adapted to detect further parameters, such as, in particular, parameters of the bioreactor, which are preferably read out from the bioreactor by means of the bioreactor cleaning system. For this purpose, an electronic interface of a bioreactor cleaning unit can be provided, via which the bioreactor cleaning system can communicate with an electronic interface of the bioreactor. Such an interface is preferably a 7-pin interface. Bioreactors typically have fixed sensors, such as level sensors or sensors that can detect a fault in the bioreactor. More contemporary bioreactors also have an interface that allows such sensors to be read out. The bioreactor cleaning system can preferably read out such sensors and thus additionally use parameters of the bioreactor to control the pump and/or valves. Preferably, the electronic control unit is further adapted to control one or more valves of the bioreactor purification system so as to control a flow of fluid through the bioreactor purification system. Preferably, it is further connected to one or more sensors of the bioreactor purification system to receive signals therefrom. In this way, it is possible to achieve further automation of the bioreactor cleaning system and improved cleaning of the bioreactor.

Furthermore, it is preferred that the bioreactor cleaning system has an acid dosing unit which has at least one acid canister connection for connecting one or more acid canisters and at least one base canister connection for connecting one or more base canisters and which can be connected to the acid tank, the freshwater connection, and the pump. The term connectable in this context means that further elements, in particular, switchable valves, may be provided between the acid dosing unit, the acid tank, the freshwater connection, and the pump. The acid dosing unit, therefore, does not necessarily have to be directly connected to the elements mentioned, but a connection via further intermediate elements is sufficient. The acid dosing unit is used to produce aqueous acid solution by mixing acid from the acid tank and freshwater from the freshwater connection, and feeding this mixture into the acid tank. It may also be used to neutralize an aqueous acid solution in the acid tank by mixing freshwater from the freshwater connection and base from the base canister(s), and then feeding this mixture to the acid tank. This may be necessary to neutralize aqueous acid solution extracted from the bioreactor for proper disposal.

Preferably, liquid can be pumped from the acid tank to the dosing unit by means of the pump. In this way, aqueous acid solution or other liquid present in the acid tank can be pumped to the acid dosing unit, where it can be mixed with acid and/or base in order to adjust the pH value of the liquid present in the acid tank. The adjustment of the pH of the liquid from the acid tank then does not take place directly in the acid tank, but in the dosing unit. In this way, continuous neutralization or continuous acidification of the liquid can be achieved. This makes it possible to adjust the pH value more precisely without provoking a pH gradient within the acid tank.

Furthermore, it is preferred that liquid can be pumped from the first suction port to the acid dosing unit by means of the pump. In this way, liquid that has been extracted from the bioreactor can first be pumped to the acid dosing unit, from where it can then be pumped either to the collection tank or to the acid tank. This makes it possible to neutralize or acidify liquid that has been extracted from the bioreactor, and to feed it to either the acid tank or the collection tank depending on whether it has been neutralized or acidified. Alternatively, neutralization of acidic liquid can be performed in the bioreactor. For this purpose, the liquid extracted from the bioreactor is pumped to the acid dosing unit as previously described in order to be enriched with base there. Then, however, the liquid is not fed into the acid tank or collection tank, but back into the bioreactor. This cycling of the liquid can continue until a neutral liquid is reached. In each case, as much base and/or acid is added as is necessary to neutralize the liquid.

In a further preferred embodiment, it is provided that liquid can be pumped from the acid tank to the collection tank by means of the pump. This is particularly preferred if there is an already neutralized or largely neutralized liquid in the acid tank, which is then transferred to the collection tank to be disposed of from there. The acid tank is then empty and ready to receive a new aqueous acid solution. Typically, the acid tank is much smaller than the collection tank. If, for example, during cleaning of a bioreactor, it occurs that the aqueous acid solution is no longer of sufficient quality to clean the bioreactor, it can be neutralized in the acid tank and then the acid tank is emptied into the collection tank. A new aqueous acid solution can then be created in the acid tank to continue the cleaning process. In this case, it is not yet necessary to empty the collection tank initially and there is no need to interrupt the cleaning process. This can shorten the cleaning time of a bioreactor, reduce throughput times, and increase the overall efficiency of the cleaning process.

Furthermore, the bioreactor cleaning system preferably has a high-pressure pump upstream of the flushing connection. Via the flushing connection, freshwater or another liquid is preferably supplied to the bioreactor under high pressure, in particular, to effect mechanical cleaning there. The high-pressure pump can be used specifically for this purpose at the flushing connection. The high-pressure pump is also preferably controlled by the electronic control unit, the electronic control unit having corresponding program code means for this purpose.

In a preferred embodiment, the bioreactor cleaning system is provided with a first valve connecting the first suction port to a second line via a first line. Preferably, a second valve is provided connecting the second line to the first pump port. Preferably, the first and second valves are connected to and can be controlled by the electronic control unit. The first suction port is connected or connectable to the first pump port via the first and second valves.

In another preferred embodiment, the bioreactor cleaning system is provided with a third valve that connects the second suction port to a fourth line via a third line. Consequently, the second suction port is connected to the third line, which is then connected to the third valve, which in turn connects the third line to the fourth line. Preferably, a fourth valve is provided which connects the fourth line to the second pump port. Thus, the second suction port is connected or connectable to the second pump port via the third and fourth valves. Preferably, the third and fourth valves are also controllable by the electronic control unit.

Preferably, a fifth valve is provided connecting the second line to the fourth line. In this way, the fifth valve forms a bypass for the pump, through which either liquid can be directed past the pump, or, on the other hand, a reversal of direction can be provided with respect to the first suction port and second suction port. Specifically, the fifth valve thus allows not only the first suction port to be connected or connectable to the first pump port, but the first suction port is also connectable to the second pump port via the fifth valve. Similarly, the second suction port is not only connectable to the second pump port, but is also connectable to the first pump port via the fifth valve.

In a preferred further development, the first pump connection is connected to the collection tank via a first collection tank valve. Here, too, it can be provided that further elements, such as valves or the like, can be provided between the collection tank and the first collection tank valve or between the first pump connection and the first collection tank valve. By switching the first collection tank valve, liquid can thus be pumped from the first pump connection into the collecting tank, or from the latter to the first pump connection.

It is also preferred that the first pump connection is connected to the acid tank via a first acid tank valve. Here too, further elements can be present between the pump connection, acid tank valve and acid tank, so that an indirect connection is also possible.

Further preferably, the second pump connection is connectable or connected to the collection tank via a second collection tank valve. Preferably, the second pump connection is also connectable or connected to the acid tank via a second acid tank valve. In this way, a circuit can also be created from the collection tank into the collection tank via the pump as well as from the acid tank into the acid tank via the pump, whereby certain further functions can be performed with respect to the liquid thus pumped, such as, in particular, measuring pH values, measuring flows, measuring volumes, and the like.

Furthermore, the bioreactor cleaning system preferably has a recirculation valve that connects the second pump connection to the acid dosing unit. Accordingly, liquid can be pumped from the second pump connection to the acid dosing unit or vice versa.

Furthermore, it is preferred that the bioreactor cleaning system has a first measuring valve that connects the second pump connection to the measuring unit. Via this first measuring valve, liquid can be pumped from the second pump connection to the measuring unit in order to measure the volume of this liquid within the measuring unit. In this way, on the one hand, certain volumes can be measured that are subsequently fed to the bioreactor, and, on the other hand, volumes that have been extracted from the bioreactor can also be measured in the measuring unit.

Preferably, a second measuring valve is provided, which connects the measuring unit to a first measuring line. The first and second measuring valves preferably open into different connections on the measuring unit, but can also open into the measuring unit at the same connection. Like the first measuring valve, the first measuring line can also lead to the second pump connection, or alternatively to the first pump connection. Preferably, however, the first measuring line does not lead directly to the first pump connection, but rather via at least one or two intermediate units, such as further valves. For example, the first measuring valve can be used to introduce liquid into the measuring unit, and the second measuring valve can be used to convey liquid out of the measuring unit.

Here, it is preferred that the bioreactor cleaning system has a sixth valve that connects the first measuring line to the fourth line. The first measuring line then opens via this sixth valve into the fourth line, via which the first measuring line can then be brought back into connection with the second pump connection, or via the fifth valve with the first pump connection.

Furthermore, the bioreactor cleaning system has a seventh valve that connects the first measuring line to the acid tank and/or collection tank. Preferably, the seventh valve connects the first measuring line to the acid tank and/or the collection tank via the second acid tank valve and/or the second collection tank valve. Consequently, the seventh valve connects the measuring line to the acid tank via the second acid tank valve and the seventh valve connects the first measuring line to the collection tank via the second collection tank valve. Between the seventh valve and the second acid tank valve or second collection tank valve, a freshwater line or a line of the dosing unit preferably opens into the line connecting these valves. It is thus possible, starting from the freshwater line or the line of the dosing unit, to convey liquid via the seventh valve into the first measuring line and thus to the measuring unit, and to feed it via the second acid tank valve to the acid tank and via the second collection tank valve to the collection tank.

In a further preferred embodiment, the bioreactor cleaning system has a level sensor in the measuring unit for detecting a quantity of liquid present in the measuring unit, the level sensor being connected to the electronic control unit and providing a measuring level signal to the latter. Via the level sensor in the measuring unit, the volume of the liquid present in the measuring unit can be detected, and a corresponding measuring level signal can be provided to the electronic control unit. Based on the signal, one or more subsequent actions can then be performed, such as performing a cleaning operation, pumping liquid from an acid tank to the second suction port, or suctioning liquid out of the bioreactor.

It is further preferred that the bioreactor cleaning system comprises a first pH sensor for detecting a first pH value of a liquid supplied to the acid tank, the first pH sensor being connected to the electronic control unit and providing a first pH signal thereto. The first pH signal can be used to determine whether the fluid supplied to the acid tank has a sufficiently low pH to be used as a fluid for chemically cleaning the bioreactor. This is relevant, on the one hand, when the aqueous acid solution is created via the dosing unit and provided in the acid tank, but also to determine whether a liquid extracted from the bioreactor has a sufficient pH value to be used a second or further time for cleaning, or whether this extracted liquid must be neutralized and disposed of.

According to another preferred embodiment, the electronic control unit comprises code means which, when executed on the electronic control unit, cause the electronic control unit to perform a cleaning procedure comprising one or more cleaning steps for cleaning and maintaining the bioreactor.

In a second aspect, the invention solves the above problem by a computer program product comprising code means which, when executed on an electronic control unit of a bioreactor cleaning system, causes it to perform a cleaning procedure comprising one or more cleaning steps for cleaning and maintaining the bioreactor, the cleaning procedure comprising: suctioning liquid from the bioreactor via a second suction port; and pumping the suctioned liquid to a collection tank.

It is to be understood that the cleaning method performed by the bioreactor cleaning system when the computer program product is executed on the control unit is also independently disclosed and claimable as a cleaning method herein. Accordingly, a cleaning method comprising one or more cleaning steps for cleaning and maintaining the bioreactor is also disclosed herein, which comprises: Suctioning liquid from the bioreactor via a second suction port; and pumping the suctioned liquid into a collection tank.

The second suction connection is preferably a connection for a 2-inch hose of a bioreactor, which can be coupled to the bioreactor cleaning system via a camlock coupling. In a bioreactor, especially in the solids tank and there in the filter basket, a filter cake is formed which should first be extracted before carrying out further cleaning steps. This is implemented in the step of suctioning liquid from the bioreactor. This liquid is pumped into the collection tank. For this purpose, the pump is preferably controlled by the electronic control unit. Likewise, one or more valves can be controlled to establish a fluid connection between the second suction port, the pump and the collection tank.

It is further preferred that the cleaning method comprises: Reading data from the bioreactor via a data connection between the bioreactor and the bioreactor cleaning system. The bioreactor cleaning system preferably has a 7-pin connection for this purpose and can read data from the bioreactor such as a last maintenance interval, fill levels, error logs, and the like. The execution of one or more cleaning steps of the cleaning process can take place depending on this read-out data. Preferably, this allows condition-based maintenance of the bioreactor to be carried out. For example, if it is determined that the last cleaning was a long time ago, six instead of four extraction cycles can be performed. The bioreactor cleaning system may also be designed to indicate on a display to an operator which steps he/she should perform manually, depending on which steps are useful and required as part of the maintenance. Such steps can also be steps that are not necessarily for cleaning alone, but can also be specific maintenance steps, such as the replacement of certain wear parts. As the operator is requested to perform these steps in the preferred embodiment, the result is also requested. Thus, a cleaning result is presented and preferably transmitted to the bioreactor, preferably at least in a case when an error-free cleaning/maintenance has been performed. Preferably, a maintenance log is generated, in particular, in the bioreactor cleaning system, which represents all or some steps and preferably the evaluation by the operator. The maintenance log is preferably evaluated by the bioreactor cleaning system and if a step was evaluated as "not ok" by the operator and/or automated, the overall maintenance result is "not ok." In this way, it can be logged exactly what was done and what was not done.

It is further preferred that the cleaning method comprises: Filling fresh water into the bioreactor via the second suction port, and waiting a predetermined first time. The purpose of filling freshwater via the second suction port, which is preferably connected to a line of the bioreactor that opens directly into the filter basket, is to soften and fluff up a filter cake present therein, so that better suction and extraction can subsequently take place. Preferably, this step is performed before the above step of suctioning liquid from the bioreactor. The steps of suctioning via the second suction port as well as filling fresh water via the second suction port can also be performed cyclically in two, three, four, five, or six cycles in order to suction the filter basket empty as much as possible. The predetermined first time can last from several seconds to several minutes, but is preferably in the range of 20 seconds to 5 minutes.

As an alternative to a data connection with the bioreactor, the bioreactor cleaning system may receive data from a station process line, or centrally, for example, from a cloud service, the bioreactor manufacturer, a fleet line, or other service provider.

However, the bioreactor cleaning system can not only read in data from the bioreactor, but preferably also switch valves of the bioreactor. This is preferably done by the electronic control unit providing corresponding signals at the electronic interface (preferably 7-pin). This makes it possible to not only clean the lines and tanks that are accessible from the outside, but also lines inside the bioreactor that only become accessible when one or more valves of the bioreactor are switched. The electronic control unit is preferably configured to provide one or more switching signals directed to the switching of one or more valves of the bioreactor at the bioreactor. The electronic control unit is further preferably adapted to cause cleaning of lines of the bioreactor, preferably as part of the cleaning procedure for the bioreactor.

Further, the cleaning method preferably comprises: Supplying a liquid to the purge port for supplying the liquid to a cleaning nozzle of the bioreactor. The supply of liquid to the flushing port is preferably performed under pressure. For this purpose, a high-pressure pump is preferably controlled by the electronic control unit so that the liquid is supplied to the cleaning nozzle under increased pressure. This is intended to clean the filter basket mechanically. The cleaning nozzle is usually permanently installed in the bioreactor and can be designed, for example, as a hollow cone nozzle or full jet nozzle. Due to the high pressure, the filter cake in the filter basket is milled off and fluffed up, so that the particles can be suctioned away in the downstream step. Therefore, this step is preferably followed by a step of suctioning liquid from the bioreactor via the second suction port. The liquid then extracted is preferably pumped into the collection tank.

It is further preferred that the method comprises: Suctioning liquid from the bioreactor via a first suction port, and pumping the suctioned liquid into the collection tank or sewer drain or into an acid tank. The first suction port of the bioreactor cleaning system is preferably connected to a 1-inch port of the bioreactor, preferably again via a camlock coupling, which opens into the liquid tank of the bioreactor. Liquid that has passed through the filter basket in the bioreactor enters the liquid tank and can be suctioned through the first suction port. Depending on what kind of liquid it is, it is either fed to the collection tank or to an acid tank. If, for example, chemical cleaning has previously been carried out with an aqueous acid solution, the extracted liquid is preferably fed to the acid tank. If it is simple water that is loaded with particles, for example, liquid that originates from a previous cleaning by means of the cleaning nozzle, the liquid extracted in this way is preferably fed to the collection tank.

In another preferred embodiment of the computer program product, the cleaning method comprises: Introducing an aqueous acid solution into the bioreactor via the first suction port and/or the second suction port and waiting a predetermined second time. Aqueous acid solution is introduced into the bioreactor to remove lime from the bioreactor. This may be necessary at the filter basket on the one hand, but also in pipes or hoses of the bioreactor on the other hand. In order to clean pipes or hoses of the bioreactor from lime, circulation of the aqueous acid solution in the bioreactor is required. In order to realize this, the process preferably comprises: Introducing compressed air into the bioreactor via the first suction port. In this way, the aqueous acid solution is forced into lines of the bioreactor so that they can be cleaned from lime deposits. These steps can also be repeated several times. The filling of the aqueous acid solution is preferably followed, after waiting for the predetermined second time, by respective suction via the first or second suction connection. The time period of the predetermined second time may be somewhat longer than the time period of the predetermined first time, in order to give the aqueous acid solution sufficient time to dissolve the lime deposits. Thus, the predetermined second time may be several minutes.

Not only can a bioreactor be cleaned via such circulation, but it is also possible to clean toilet tanks and their pipes in train carriages. For this purpose, the bioreactor cleaning system can be connected to connections provided for this purpose on the respective wagon. However, depending on the structure of the wagon, it may also be conceivable and preferred that the bioreactor cleaning system switches certain valves in the wagon in order to clean the toilet tanks and their lines. This can be done, for example, by means of the electronic interface, via which the electronic control unit can provide corresponding signals.

Preferably, the cleaning method further comprises: Introducing an aqueous acid solution into the bioreactor via the second suction port and simultaneously suctioning liquid out of the bioreactor via the first suction port. In this way, aqueous acid solution can be circulated through the bioreactor. It is supplied via the second suction port, then from there—when properly connected to the bioreactor—it is introduced into the filter basket, passes through the latter into the liquid reactor, and is extracted out of the liquid reactor into the bioreactor cleaning system. There, the aqueous acid solution can be pumped directly back to the second suction connection without being fed into the acid tank.

If the aqueous acid solution is to be neutralized, this can also be done in the bioreactor itself. For this purpose, the aqueous acid solution is circulated through the bioreactor as described, and then conveyed to or through the metering unit in the bioreactor cleaning system, where an appropriate volume of base is then added to neutralize the aqueous acid solution. If the aqueous acid solution is neutralized in the bioreactor rather than in the acid tank, the neutralized liquid can be drawn from the bioreactor after neutralization is complete and sent either to the collection tank or directly to a sewer drain for disposal.

It is further preferred that the cleaning method comprises: Measuring a predetermined volume of liquid in a measuring unit; supplying a predetermined volume of liquid into the bioreactor via the second suction port; waiting a predetermined third time; suctioning liquid from the bioreactor via the first suction port; supplying the suctioned liquid to the measuring unit; and measuring the volume of the suctioned liquid. These steps can be used to test a permeability of the bioreactor. The volume of the suctioned or extracted liquid that is measured should ideally be the same as the predetermined volume of liquid supplied. If there is a difference here that exceeds a predetermined threshold, this indicates a lack of permeability of the bioreactor. In this case, further cleaning should be carried out. It may also be envisaged that, if the measurement in the measuring unit shows that the difference does not fall below the threshold value, a signal is output via a human-machine interface indicating that the cleaning process was successful. Otherwise, a signal can be output indicating that the cleaning process was not successful.

Preferably, the cleaning method further comprises: Cleaning a sanitizing unit of the bioreactor. Cleaning of the sanitizing unit may comprise the same or similar steps as cleaning of the bioreactor. Preferably, the flushing connection is first connected to the bioreactor and/or the sanitizing unit if it has its own high pressure connection with cleaning nozzle. If not, this equipment is preferably manually attached to the sanitizing unit and connected to the flushing connection of the bioreactor cleaning unit. If separate drain valves are provided for the sanitizing unit, these must be opened. In the event that the sanitizing unit can be drained via the bioreactor, this is generally done via the suction connection of the bioreactor cleaning system, although this can also be connected to a separate connection of the sanitizing unit as part of the cleaning of the sanitizing unit. Cleaning the sanitizing unit then comprises: Supplying liquid to the flushing connection for supplying the liquid to a cleaning nozzle of the sanitizing unit. Further, cleaning the sanitizing unit preferably comprises: Suctioning liquid from the sanitizing unit via the first suction port of the bioreactor cleaning unit or a third suction port provided therefor. Feeding and suctioning are preferably performed simultaneously so that a high-pressure jet from the cleaning nozzle can impinge on surfaces of the sanitizing unit without hindrance. When sufficient cleaning has been performed with the nozzle and/or a predetermined time has been reached, the supply of liquid to the rinsing connection is stopped and liquid continues to be extracted from the sanitizing unit, preferably for at least a predetermined period of time. Valves can then be closed and hoses disconnected again, if necessary.

Embodiments of the invention are now described below with reference to the drawings. These are not necessarily intended to show the embodiments to scale; rather, where useful for explanation, the drawings are in schematized and/or slightly distorted form. With regard to additions to the gauges directly recognizable from the drawings, reference is made to the relevant prior art. It should be borne in mind that a wide variety of modifications and changes concerning the shape and detail of an embodiment can be made without departing from the general idea of the invention. The features of the invention disclosed in the description, in the drawings as well as in the claims may be essential for the further development of the invention both individually and in any combination. In addition, all combinations of at least two of the features disclosed in the description, the drawings and/or the claims fall within the scope of the invention. The general idea of the invention is not limited to the exact form or detail of the preferred embodiments shown and described below, or limited to any subject matter that would be limited as compared to the subject matter claimed in the claims. In the case of stated design ranges, values lying within the stated limits are also intended to be disclosed as limiting values and to be capable of being used and claimed as desired. For simplicity, identical reference signs are used below for identical or similar parts or parts with identical or similar function.

BRIEF DESCRIPTION OF THE DRAWINGS

Further advantages, features, and details of the invention will be apparent from the following description of preferred embodiments and from the drawings. The drawings show in.

DETAILED DESCRIPTION OF THE EMBODIMENTS

Figure 1:
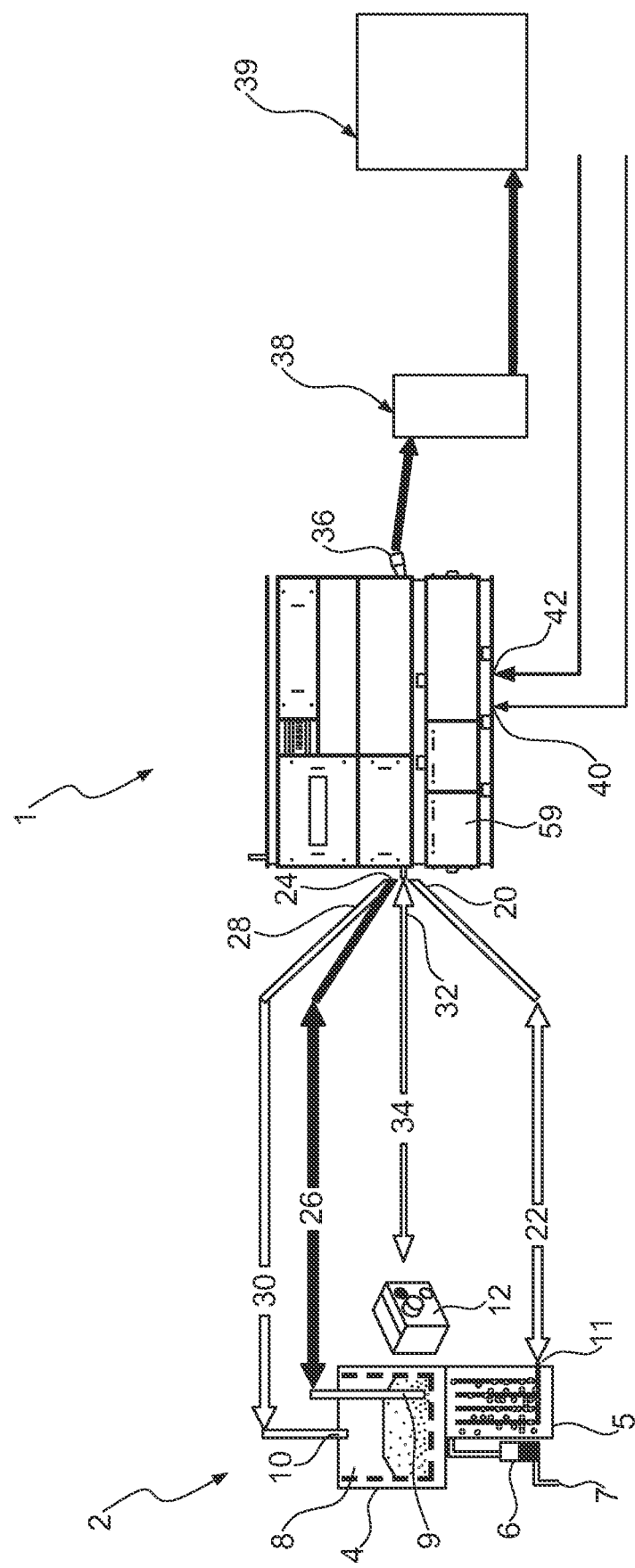
FIG. 1 is a schematic representation of the bioreactor cleaning system in connection with a bioreactor as well as further elements.

A bioreactor cleaning system 1 can be designed as a mobile bioreactor cleaning system, as shown in FIG. 1, or as a stationary bioreactor cleaning system. A mobile bioreactor cleaning system can typically be moved to a train in which a bioreactor 2 is arranged. Bioreactors 2 in trains are generally known and will not be further described in detail here. In FIG. 1, a vertically oriented bioreactor 2 is shown as an example, with a solids tank 4, a liquid tank 5, and a sanitizing unit 6, which has an outlet 7, for draining liquid. A filter basket 8 is provided in the solids tank 4, into which both a 2-inch hose 9 terminates near the bottom, and a cleaning nozzle 10 is provided to supply water under high pressure to the solids tank 4 to clean off a filter cake built up in the filter basket 8. A 1-inch connection 11 is further provided at the liquid tank 5 to draw liquid from or supply liquid to the liquid tank 5. Further, the bioreactor 2 comprises a controller 12 that can, for example, read sensors of the bioreactor 2.

The bioreactor cleaning system 1 has connections via which it can be connected to the bioreactor 2. For example, in order to extract liquid from the bioreactor 2, the bioreactor cleaning system 1 has a first suction connection 20, which can be connected to the 1-inch connection 11 of the liquid tank 5 of the bioreactor 2 via a first suction line 22. Furthermore, the bioreactor cleaning system 1 has a second suction connection 24, which can be connected to the 2-inch hose 9 of the bioreactor 2 via a second suction line 26, in order to suction off liquid from the bioreactor 2, more specifically the solids tank 4, via this hose in order to remove filter cake formed therein. However, liquid can also be added to the bioreactor 2 via the 2-inch hose 9 for cleaning purposes, as will be described in more detail below. The bioreactor cleaning system 1 also has a high-pressure connection 28, which can be connected to the cleaning nozzle 10 via a high-pressure hose 30, and an electronic control connection 32, which can be connected to the control 12 of the bioreactor 2 via a signal line 34.

The bioreactor cleaning system 1 further comprises a disposal connection 36, via which the bioreactor cleaning system 1 can be connected to an external tank 38 or a sewer system, which is connected to an external vacuum source 39, so as to extract liquid from the bioreactor cleaning system 1. On the input side, the bioreactor cleaning system 1 has a power connection 40 and a freshwater connection 42.

Figure 2:
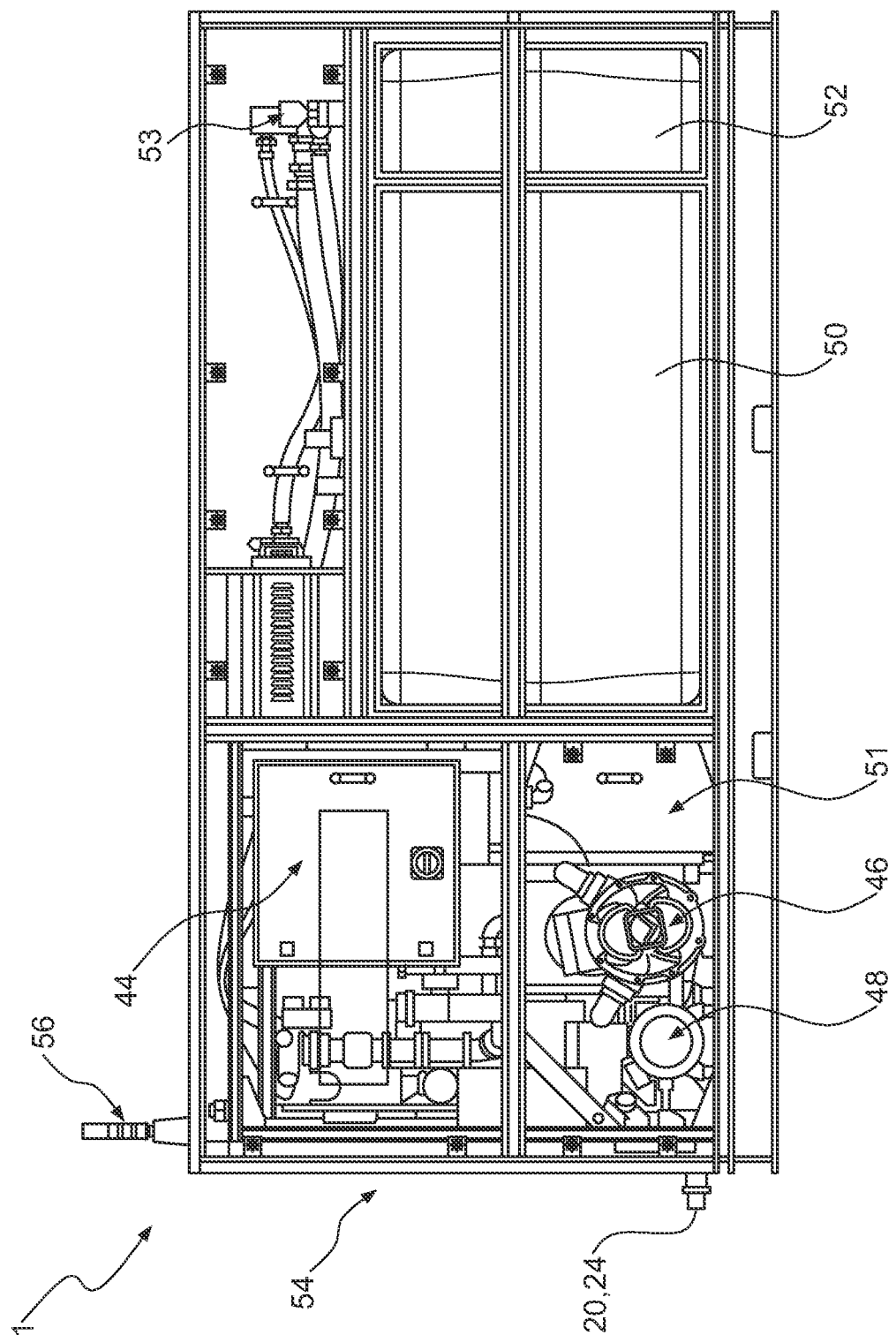
FIG. 2 is a schematic side view of the bioreactor cleaning system, partially cut free.

Inside the bioreactor cleaning system 1 (FIG. 2), an electronic control unit 44 which has a memory with program code and a processor for executing the program code is provided. The electronic control unit 44 controls various functions of the bioreactor cleaning system 1, as will be apparent, in particular, from the further description. For example, the electronic control unit 44 controls a pump 46 as well as a high pressure pump 48. The pump 46 can be used to provide a vacuum at the first suction port 20 or the second suction port 24 as well as to pump fluid to the second suction port 24. The high pressure pump 48 is used to provide a fluid at high pressure to the high pressure port 28. Furthermore, a collection tank 50 and an acid tank 52 are provided inside the bioreactor cleaning system 1, wherein a first level sensor 51 is provided for the collection tank 50 and a second level sensor 53 is provided for the acid tank 52. On the left-hand side of the bioreactor cleaning system 1 in FIG. 2, a human-machine interface 54 is arranged, which comprises, for example, a touch display. Via this human-machine interface 54, for example, the electronic control unit 44 can be operated and, for example, parameters or the like can be entered. Also, a cleaning program or a precise sequence of a cleaning procedure can be selected via the human-machine interface 54. A warning light 56 is optionally provided on an upper side of the bioreactor cleaning system 1, which is adapted to emit light in different colors for indicating a status, a fault, or the like of the bioreactor cleaning system 1.

Figure 3:
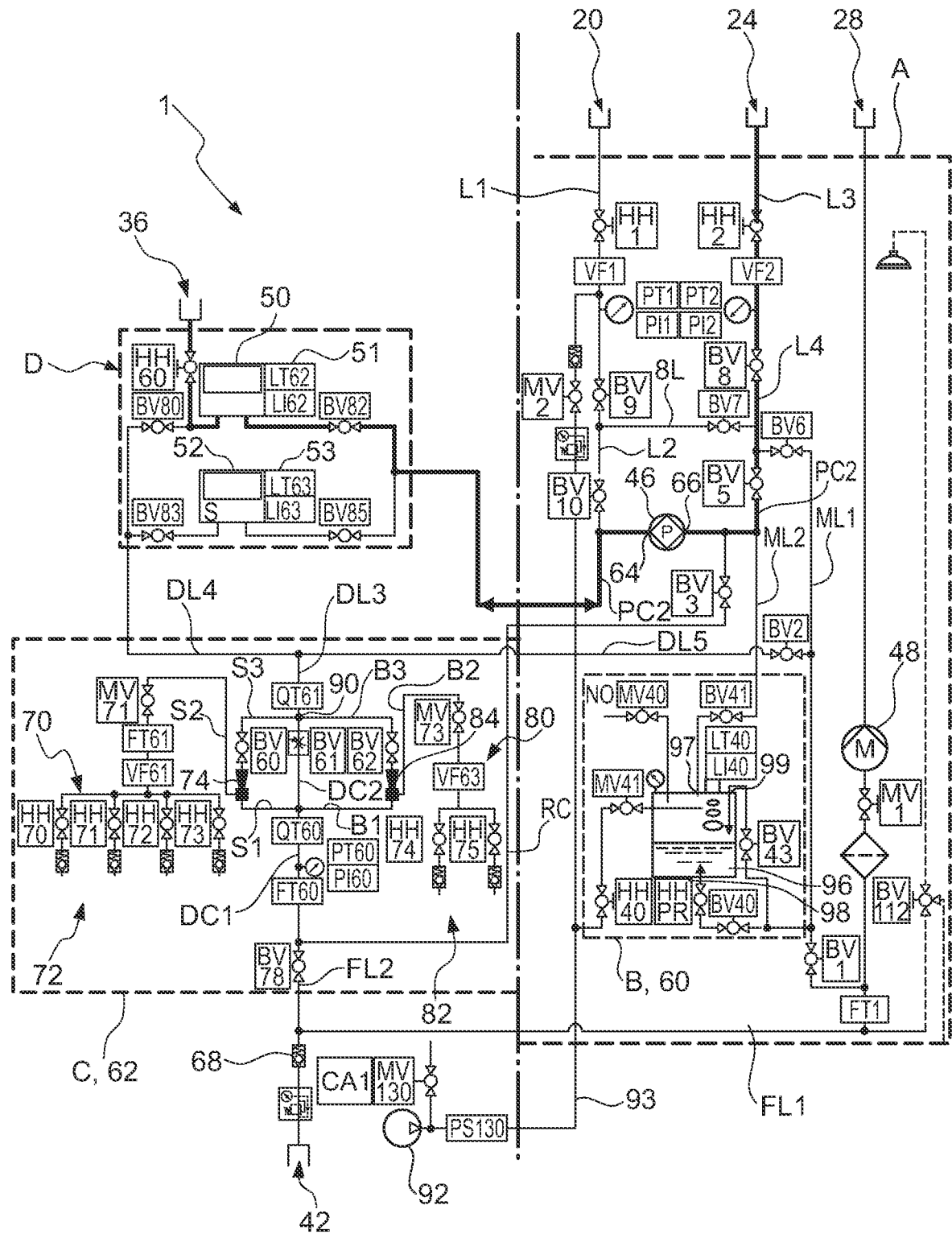
FIG. 3 is a circuit diagram of the bioreactor cleaning system.

FIG. 3 now shows a complete layout or circuit diagram of the mobile bioreactor cleaning system 1, in which the pump 46 as well as the first suction port 20, the second suction port 24, the flushing port 28, the disposal port 36, and the freshwater port 42 are shown. Furthermore, the high-pressure pump 48 is shown. Not shown in FIG. 3 are the electronic connections as well as the electronic control unit 44, but it is to be understood that the electronic control unit 44 is actually connected to the pump 46 as well as the high pressure pump 48, and also to some or all of the other valves and sensors described below. The layout of a stationary bioreactor cleaning system may differ slightly in details, but the functionality is essentially the same and stationary bioreactor cleaning systems are also encompassed by the invention.

In FIG. 3, the bioreactor cleaning system 1 is shown subdivided into four systems, namely a system A, which includes the pump 46 as well as the high-pressure pump 48, and which also includes the first and second suction ports 20, 24, as well as the flushing port 28. A system B is shown within system A and includes a metering unit 60, which will be described in more detail. System C includes an acid dosing unit 62, and system D includes collection tank 50, acid tank 52, corresponding associated level sensors 51, 53, and disposal port 36.

Pump 46 has a first pump port 64 and a second pump port 66, and pump 46 is preferably configured as a rotary lobe pump and is able to pump fluid from the first pump port 64 to the second pump port 66 as well as vice versa from the second pump port 66 to the first pump port 64.

A first line L1 extends from the first suction port 20 in the direction of the first pump port 64. The first line L1 is connected to a first valve BV9, which in turn is connected to a second line L2. First valve BV9 is designed as an electrically switchable ball valve and can be controlled by the electronic control unit 44. Other types of valves, such as switching valves, are also preferred. Now, it is important in the context of the invention that some of the valves are electrically switchable by the electronic control unit 44. A ball valve has the advantage that the flow through the valve is continuously adjustable. Furthermore, in the embodiment shown, a first manual valve HH1 is placed in first line L1, which allows manual opening and closing of first line L1. A first capacitive sensor VF1 is also provided between first valve BV9 and first manual valve HH1, which senses the presence of fluid in the first line L1 and provides a signal representing the presence of fluid in the first line L1 to the electronic control unit 44.

Here, second valve BV10 is connected to first pump connection 64, more specifically to a first pump line PL1 that originates from the first pump connection 64. With reference to FIG. 3, the first pump line PL1 runs to the left to system D.

Second suction port 24 is connected to a third line L3, which is connected to a fourth line L4 via a third valve BV8. Again, a second manual valve HH2 is placed in third line L3, which allows manual opening and closing of third line L3. A second capacitive sensor VF2 is placed between second manual valve HH2 and third valve BV8, which also detects the presence of fluid there and provides a corresponding signal representing the presence of fluid to the electronic control unit 44. A first pressure sensor PT1 is also provided in first line L1 and a second pressure sensor PT2 is provided in third line L3, which detect pressure in first and third lines L1, L3 and provide corresponding first and second pressure signals to the electronic control unit 44. Fourth line L4 is connected to the second pumping port 66 via a fourth valve BV5, more specifically to a second pumping line PL2. Second pump line PL2 connects second pump port 66 to fourth valve BV5.

According to the embodiment shown here, a bypass is provided between second line L2 and fourth line L4, namely, in the form of a bypass line BL, which can be closed by a fifth valve BV7. Bypass line BL is used to allow not only the first suction port 24 to be connectable to the first pump port 64 via first line L1 and second line L2, but the first suction port 20 is also connectable to the second pump port 66 via first line L1, bypass line BL, and fourth line L4. In a corresponding manner, second suction port 24 is also connectable to second pump port 66 not only via third and fourth lines L3, L4, but also via third line L3, bypass line BL, second line L2, and first pump line PL1. Depending on the directions in which liquids are to be pumped, this is advantageous.

If, for example, liquid is suctioned or extracted from the bioreactor 2 in a first cleaning step, this is done via the second extraction port 24. For this purpose, the second manual valve HH2 is to be opened, at the same time electronic control unit opens the third valve BV8 and the fourth valve BV4 and the pump conveys the extracted liquid from the second pump port 66 to the first pump port 64 in the first pump line PL1. Second valve BV10 is closed and the liquid flows through first pump line PL1 toward the system D. In system D, collection tank 50 is connected to first pump line PL1 via a first collection tank valve BV82 and acid tank 52 is connected to first pump line PL1 via a first acid tank valve 85. Thus, in order to convey the extracted liquid from the second extraction connection 24 into the collection tank 50, electronic control unit 44 also opens the first collection tank valve 82. If liquid is now additionally to be extracted from the liquid tank 5 of the bioreactor 2 via first extraction connection 20, first manual valve HH1 must be opened. Electronic control unit 44 then opens first valve BV9, fifth valve BV7, and fourth valve BV5. In this way, the first suction port 20 is connected to the second pump port 66. Pump 46 can then, in turn, pump from the second pumping port 66 to the first pumping port 64, thereby delivering the fluid extracted via first suction port 20 to collection tank 50 via the first collection tank valve 82.

Collection tank 50 is emptied into the disposal tank 38 or into the sewer system via a third manual valve HH50, which connects collection tank 50 to disposal connection 36.

Especially in system D, differences exist between the mobile bioreactor cleaning system 1 shown here and a stationary bioreactor cleaning system. For example, a separate additional pump may be provided for emptying collection tank 50 and acid tank 52, preferably in the form of a double pump. Furthermore, another pump is preferably provided, again in the form of a double pump, for filling acid tank 52 with acid and for filling the acid from the acid tank into the respective connected bioreactor. By means of the further pump, in this case, circulation of the liquid through the bioreactor can also be carried out. In addition, a stationary system can have an additional connection for providing freshwater for a catering service in the train or wagon, as well as another additional connection for providing freshwater for hand washing and/or toilet flushing. A branch line for this additional connection preferably branches off directly from the freshwater connection 42, so that no contamination can take place here.

Also connected to fourth line L4 is a sixth valve BV6, which connects fourth line L4 to a first measuring line ML1. First measuring line ML1 leads on the one hand to the measuring unit 60, and on the other hand also to an eighth valve BV1, which is connected to a first freshwater line FL1 via a first flow sensor FT1. First freshwater line FL1 is connected to the freshwater connection 42 via a check valve 68 and thus receives freshwater from the freshwater connection 42. If, for example, freshwater is to be fed into the filter basket 8 of bioreactor 2 via second suction connection 24, eighth valve BV1, sixth valve BV6, and third valve BV8 must be opened for this purpose. Freshwater is already provided under a certain pressure via the freshwater connection 42, and can thus be fed directly into the bioreactor 2 with sufficient pressure. However, if freshwater under increased pressure is to be supplied to cleaning nozzle 10 via flushing connection 28, a ninth valve MV1, which is designed here as a solenoid valve, must first be opened for this purpose. Ninth valve MV1 connects first freshwater line FL1 downstream of first flow sensor FT1 to high-pressure pump 48, which can then supply freshwater under high pressure to flushing connection 28. Ninth valve MV1 and high pressure pump 48 are also controlled by electronic control unit 44.

Freshwater port 42 is further connected to acid dosing unit 62 via a second freshwater line FL2. Acid dosing unit 62 includes a plurality of acid canister ports 70, and a plurality of base canister ports 80. Acid canister ports 70 are connected to acid canisters 72, and base canister ports 80 are connected to base canisters 82. Acid and base canisters 72, 82 can be interchanged, and are stored, for example, at the lower portion of the bioreactor cleaning unit 1. Second freshwater line FL2 leads to a tenth valve BV78, and from there to a second flow sensor FT60. Downstream of second flow sensor FT60, a third pressure sensor PT60 and a first pH sensor QT60 are provided. Second flow sensor FT60, third pressure sensor PT60, and first pH sensor QT60 can be used to detect values of the fluid present in first dosing line DL1. Downstream of first pH sensor QT60, first dosing line DL1 branches into an acid line 51, a second dosing line DL2, and a first base line B1. First acid line 51 leads to an acid doser 74, which is designed here as an acid ejector and, in addition to liquid from first dosing line DL1 or first acid line 51, also receives undiluted acid via a second acid line S2, which is connected to the acid canister connections 70. An eleventh valve MV71, which is designed as a solenoid valve, is placed in second acid line S2. It serves to seal off the acid canister connections 70 from second acid line S2. Downstream of acid doser 74, a twelfth valve BV60 is provided, which is again designed as a ball valve and is again controlled by the electronic control unit 44. Twelfth valve BV60 connects acid doser 74 to a third acid line S3, which leads to a mixer 90. Mixer 90 may comprise, for example, a static mixer having a mixing element.

On the other side, first base line B1 connects second flow line DL2 to a base dosing unit 84, which is designed here as a base ejector. Base dosing unit 84 receives not only liquid via first base line B1, but also undiluted base via a second base line B2. A thirteenth valve MV73 is placed in second base line B2, which is formed as a solenoid valve, and is controlled by electronic control unit 44. Thirteenth valve MV73 serves to seal off the base canister connections 80 from second base line B2 or base doser 84. Downstream of the base doser 84, a fourteenth valve BV62 is provided, which is again a ball valve and is controlled by electronic control unit 44. Fourteenth valve BV62 connects base doser 84 to a third base line B3, which also opens into the mixer 90. Thus, a fluid having a specific pH can be created in mixer 90 via this arrangement. Downstream of mixer 90, mixer 90 opens into a third dosing line DL3 in which a second pH sensor QT61 is placed to provide a second pH signal to electronic control unit 44. Third dosing line DL3 branches into a fourth dosing line DL4, which leads to acid tank 52 or collection tank 55, and a fifth dosing line DL5, which leads back to system A. Fourth dosing line DL4 is connected to a second acid tank valve BV83 and a second collection tank valve BV80, so that liquid from fourth dosing line DL4 can be selectively fed to acid tank 52 or collection tank 50 via second acid tank valve BV83 and second collection tank valve BV80. This is particularly important if an aqueous acid solution is to be created in acid tank 52. To this end, electronic control unit 44 controls tenth valve BV78, eleventh valve MV71, twelfth valve BV60, fourteenth valve BV62, and thirteenth valve MV73 such that a liquid having a predetermined desired pH can be provided in fourth dosing line DL2 and thus enter acid tank 52.

Aqueous acid solution is used, in particular, to chemically clean bioreactor 2 so as to remove lime deposits in it. For this purpose, aqueous acid solution must be fed from acid tank 52 to first and/or second suction ports 20, 24. This is effected by pump 46, which is connected to acid tank 52 in an appropriate manner. For example, if aqueous acid solution is to be provided to first suction port 20, electronic control unit 44 opens first acid tank valve BV85, fourth valve BV5, fifth valve BV7, and first valve BV9. Aqueous acid solution is then provided via first pump line PL1, from first pump port 64 to second pump port 66 and via the aforementioned valves to first suction port 20. In a corresponding manner, aqueous acid solution can also be provided at second suction port 24, in which case, in deviation from the aforementioned, fifth and first valves BV7, BV9 do not have to be opened, but instead only third valve BV3.

If an aqueous acid solution has been used to clean bioreactor 2, it is also necessary to extract it again from the bioreactor 2. This is done via the first suction port 20. If an aqueous acid solution is sucked out of the bioreactor 2 via suction port 20, first valve BV9, fifth valve BV7, fourth valve BV5, and first acid tank valve BV85 are opened for this purpose. Pump 46 then pumps the aqueous acid solution from second pump port 66 to first pump port 64, and consequently into acid tank 52.

If the aqueous acid solution in acid tank 52 is to be neutralized, electronic control unit 44 controls acid dosing unit 62 accordingly to provide a liquid suitable for neutralizing the aqueous acid solution in acid tank 52. It is also possible to achieve pass-through or continuous neutralization. For this purpose, aqueous acid solution is drawn from acid tank 52 via first acid tank valve 85 by means of pump 46, pumped from first pumping port 64 to second pumping port 66, and from there via a return valve BV3 connecting second pumping line PL2 or second pumping port 66 to acid dosing unit 62. More specifically, a return line RL leads from return valve BV3 to second fresh water line FL2 and opens into it downstream of tenth valve BV78 but upstream of first flow meter 60. By means of first pH sensor QT60, the pH of the aqueous acid solution thus recycled from acid tank 52 can then be determined and valves BV60, BV62 and a throttle BV61 can be controlled so that sufficient base is added to the aqueous acid solution provided through recycle line RL3 to neutralize it. After the solution has been neutralized in acid tank 52, it can be conveyed to collection tank 50 by means of pump 46.

To improve the cleaning of bioreactor 2 with aqueous acid solution, air can also be introduced into the aqueous acid solution in the form of bubbles via first suction port 20. For this purpose, a compressor 92 is provided, which is connected to first line L1 via a compressor line 93 and a compressor valve MV2, and can thus feed compressed air into first line L1. Compressor 92 and first compressor valve MV2 can also be controlled by electronic control unit 44.

Measuring unit 60 is now constructed and connected to the further elements as follows: Measuring unit 60 comprises a measuring chamber 96 with a first port 97, a second port 98, and a third port 99. First port 97 is connected to second pump line PL2 via a first measuring valve BV41, in particular, via a second measuring line ML2. Second port 98 is connected to first measuring line ML1 via a second measuring valve BV40, and third port 99 is also connected to first measuring line ML1 via a third measuring valve BV43. A level sensor LT40 is further provided for the measuring chamber 96, which is connected to electronic control unit 44 and can provide a measuring level signal thereto. The measuring unit 60 is used to test the permeability of bioreactor 2 after a cleaning has been performed. For this purpose, a predetermined volume of freshwater is first measured in the measuring chamber 96. This is preferably done by opening eighth valve BV1 and second measuring valve BV40. In this way, freshwater can flow through second port 98 into the measuring chamber 96 until a predetermined volume is reached, which is determined by means of the measuring level signal.

After the predetermined volume has been measured in the measuring chamber 96, it can be supplied to bioreactor 2 via second suction port 24. For this purpose, first measuring valve BV41 is opened, the liquid is pumped from second pumping port 66 to first pumping port 64, then further via second valve BV10, bypass line BL, fifth valve BV7, as well as third valve BV8 to second suction port 24. Subsequently, a predetermined time is waited until the liquid has passed through bioreactor 2. Subsequently, the liquid is extracted from the liquid tank 5 via first suction port 20 by opening first valve BV9 and second valve BV10, the liquid is pumped from first pumping port 64 to second pumping port 66 and then introduced into the measuring chamber 96 via fourth valve BV5, sixth valve BV6, and third measuring valve BV43. There, the extracted fluid is measured again. If the volume difference between the supplied liquid and the extracted liquid does not exceed a predetermined threshold, the cleaning is okay. If the volume difference exceeds a predetermined threshold, the cleaning is not okay and a corresponding warning signal can be output, for example, via warning light 56 and/or human-machine interface 54. The comparison of whether or not the volume difference exceeds the predetermined threshold is preferably performed by electronic control unit 44.

Figure 4:
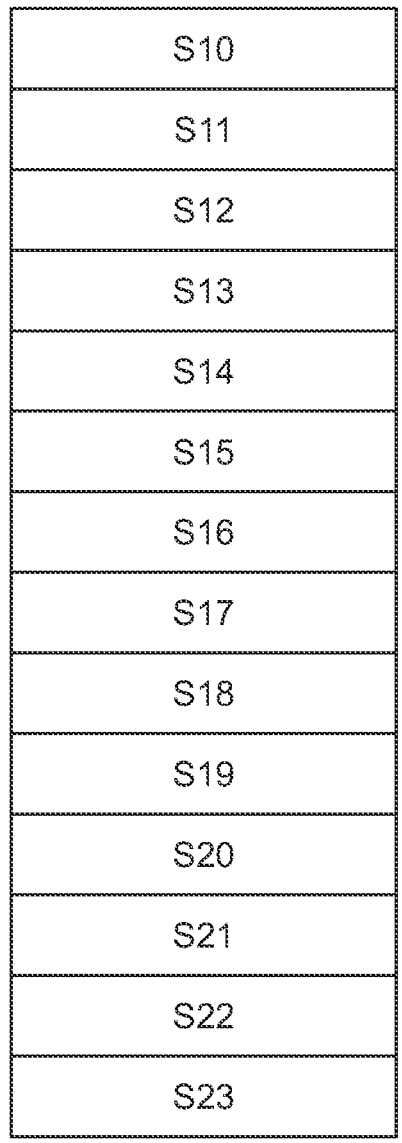
FIG. 4 is a first embodiment of a cleaning process.

With reference to FIG. 4, a first embodiment of a cleaning process according to the invention is now illustrated. The cleaning method is disclosed as such herein. However, it is to be understood that the computer program according to the invention, which may be stored and/or executed on the control unit 44 of the bioreactor cleaning system 1, causes the bioreactor cleaning system 1 to perform the cleaning procedure. The cleaning procedure explained in FIG. 4 may comprise, for example, twenty-eight steps, although the procedure may also comprise more or fewer steps. The cleaning procedure basically works cyclically and can be performed as a mechanical cleaning procedure, in which no acid is introduced into bioreactor 2, or as a chemical cleaning procedure, in which acid is used to clean bioreactor 2.

In step S10, freshwater is first introduced into bioreactor 2 from freshwater connection 42 via second suction connection 24. For this purpose, electronic control unit 44 switches the corresponding valves and controls pump 46, as basically described above. In this first step S10, preferably about 50 liters of water are introduced into bioreactor 2. This should take about 1 minute. In step S11, liquid is then extracted from the bioreactor 2 via second suction port 24 and pumped into collection tank 50. Also for this purpose, electronic control unit 44 controls the corresponding valves and pump 46. This is preferably carried out until the second capacitive sensor VF2 detects that there is no more liquid in line L3. Step S12 is then optional and in this step liquid is extracted from the bioreactor via first suction port 20. This is not mandatory, but can be implemented to clean the bioreactor of this liquid. Subsequently, in step S13, liquid, preferably freshwater, is again added to bioreactor 2 via second suction port 24. Liquid can also be added to bioreactor 2 via first suction port 20 in step S15. Both serve to flush up solids in bioreactor 2. In step S16, preferably additional mechanical cleaning is then carried out by providing freshwater under high pressure via flushing connection 28. For this purpose, electronic control unit 44 controls the corresponding valves, namely, in particular ninth valve MV1 as well as high-pressure pump 48. During this flushing with high pressure, preferably only 40% of the bioreactor volume is to be filled with water. Depending on the bioreactor 2, this can correspond to a volume of approximately 70 to 100 liters.

In step S17, liquid is then again extracted from bioreactor 2 via second suction port 24, and in step S18, liquid is also extracted via the first extraction port 20. In both step S17 and step S18, extraction preferably continues until the first and second capacitive sensors VF1, VF2 detect that there is no liquid left in first and third lines L1, L3, respectively. Steps S19 to S23 are then preferably repetitions of steps S14 to S18 and may be repeated as many times as necessary to achieve sufficient cleaning. However, it may be envisaged that higher filling levels of the bioreactor 2 are also allowed in the subsequent steps in which liquid is provided via flushing port 28, for example 60, 70, or 80%. It can also be provided that in step S18 as well as in step S23, initially no suction is provided via first suction port 20, but that this liquid remains inside bioreactor 2. Only in the last step, before the process is terminated, suction is applied via first suction port 20 in order to completely empty bioreactor 2, namely also in particular the liquid tank 5.

Figure 5:
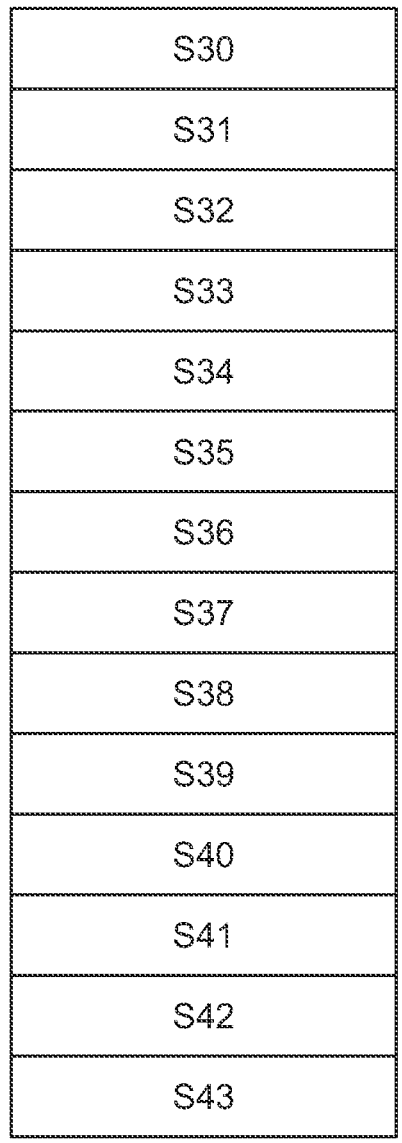
FIG. 5 is a second embodiment of a cleaning process.

FIG. 5, on the other hand, illustrates a chemical cleaning process and thus a further example of an embodiment of the cleaning process. However, it should be understood that the mechanical cleaning process according to FIG. 4 can also be combined with the cleaning process according to FIG. 5. For example, the mechanical cleaning process according to FIG. 4 may be carried out as a first part of the cleaning process, followed by the chemical cleaning process according to FIG. 5.

In step S30, an aqueous acid solution, which has already been provided in acid tank 52, is supplied to bioreactor 2 via first suction port 20. Subsequently, aqueous acid solution is also supplied to bioreactor 2 via second suction port 24. This can also be done simultaneously with step S30. Alternatively, it is also possible to perform step S31 before step S30. Subsequently, after the aqueous acid solution has been introduced into bioreactor 2, a waiting time takes place in step S32. This is preferably at least 5 minutes, preferably it is in the range of 5 minutes to 1 hour, preferably 20 minutes to 30 minutes. This is a sufficient time to clean lime deposits to a large extent. Subsequently or simultaneously, compressed air can also be introduced into bioreactor 2 by means of compressor 92 in step S33. Compressor 92 is also controlled by electronic control unit 44 so that it provides an appropriate signal to it in step S33. In step S34, a circulation of aqueous acid solution through bioreactor 2 can then be carried out. For this purpose, aqueous acid solution is preferably introduced into bioreactor 2 via second suction port 24 and extracted via the first suction port 20. For this purpose, electronic control unit 44 preferably opens first valve BV9, second valve BV10, fourth valve BV5, and third valve BV3. Pump 46 is driven to pump the fluid from first pump port 64 to second pump port 66. In this manner, circulation of the aqueous acid solution through bioreactor 2 can be effected. During this circulation, air can additionally be bubbled into the liquid, preferably by means of compressor 92. The air bubbles in the liquid cause mechanical cleaning of the lines as well.

However, it is also possible to pass the aqueous acid solution that has been extracted from bioreactor 2 via first suction port 20 through acid dosing unit 62, for example, to dose in additional acid.

In step S35, a pause is made and a certain time is waited. This time is again used to allow the aqueous acid solution to act in order to dissolve the lime deposits. It can be of a similar time range as mentioned above, preferably again in the range of 20 to 30 minutes. Then, in step S36, compressed air is preferably again introduced through first suction port 22, and in step S37, the aqueous acid solution is circulated in bioreactor 2. Steps S35 to S37 may then follow this several times, so that several cycles of pause (step S35), introduction of compressed air (S36) and circulation of the aqueous acid solution in bioreactor 2 (S37) are carried out. For example, five cycles of this can be performed.

Then, in step S38, the aqueous acid solution is extracted from bioreactor 2 via first suction port 20 and supplied to acid tank 52. This is effected by means of pump 46 by opening first valve BV9, fifth valve BV7, fourth valve BV5, and first acid tank valve BV85. Pump 46 then pumps the aqueous acid solution from second pump port 66 to first pump port 64 and into acid tank 52. To then rinse the bioreactor of residual acid, freshwater is preferably introduced both in step S39 via second suction port 24 and in step S40 via first suction port 20. Optionally, fresh water is also introduced via flushing port 28. This water thus supplied for rinsing is preferably subsequently extracted in step S41 and step S42 via first and second suction ports 20, 24 and pumped into collection tank 50.

As an alternative to this neutralization within acid tank 52, neutralization can also be carried out in bioreactor 2 itself. This can save freshwater for rinsing.

For this purpose, the aqueous acid solution to be neutralized is preferably first suctioned out of bioreactor 2 into the acid tank 52, preferably via first suction connection 22. Freshwater is then preferably introduced into bioreactor 2 in order to rinse it for a first time. This can be done either via flushing port 28 or via second suction port 24. The liquid then present in the bioreactor is acidic and must be further neutralized. The liquid can now be extracted via first suction port 20, and passed over the acid dosing unit, where it is mixed with base, and fed back into bioreactor 2. This cycle or cycling can be repeated until a sufficiently neutral pH is achieved. Subsequently, the neutralized liquid can be suctioned out of the bioreactor 2, preferably via first suction port 22, and then either fed into collection tank 50 or directly into a sewer drain for disposal. In this way, bioreactor 2 is filled with freshwater only once for rinsing, whereas it would have to be rinsed several times if the liquid used for rinsing had to be neutralized in the acid tank 52 after each rinse. This procedure is particularly efficient for mobile bioreactor cleaning systems that have base canisters containing high doses of base. In stationary systems, on the other hand, diluted base is generally used to make the tubing or piping between the bioreactor cleaning system and the bioreactor easier to carry out.

Simultaneously or subsequently, the aqueous acid solution in acid tank 52 can be neutralized or first tested for its pH content. If the aqueous acid solution is extracted from bioreactor 2 via first suction port 20, it is also conceivable not to pump it directly into acid tank 52, but rather by opening valves BV9, BV10, BV3, to feed it to acid dosing unit 60 and from there via second acid tank valve BV83 into acid tank 52.

The individual steps described herein may also be performed in other sequences, in other combinations, or multiple times. This may be performed based on sensor data or parameters sensed by electronic control unit 44. For example, the number of repetitions of a circulation of the aqueous acid solution (steps S35 to S37) may be carried out depending on the type of bioreactor read out from the bioreactor by electronic control unit 44. Other parameters that may have an influence on this are also the past of the last cleaning interval, the operating age of the bioreactor, and the like.

The invention claimed is:

1. A bioreactor cleaning system for cleaning a bioreactor, comprising:
    a first suction connection for connecting to the bioreactor;
    a second suction connection for connecting to the bioreactor, via which a liquid can be suctioned out of a filter basket of the bioreactor;
    a flushing connection for supplying a liquid to a cleaning nozzle of the bioreactor;
    an acid tank for receiving an aqueous acid solution;
    a collection tank for collecting liquid extracted from the bioreactor;
    a fresh water connection for supplying the bioreactor cleaning system with fresh water;
    a pump having a first pump port and a second pump port; and
    a measuring unit for measuring liquid; whereby by means of the pump:
        liquid can be pumped from the first suction connection selectively into the measuring unit, into the collecting tank or into the acid tank;
        aqueous acid solution can be pumped from the acid tank to the second suction connection and/or to the flushing connection;
        fresh water can be pumped from the fresh water connection selectively to the flushing connection or the measuring unit; and
        liquid can be pumped from the measuring unit either to the collection tank or to the second suction connection.

2. The bioreactor cleaning system of claim 1, wherein the bioreactor is in a rail vehicle.

3. The bioreactor cleaning system of claim 1, wherein the pump is a rotary lobe pump.

4. The bioreactor cleaning system of claim 1, including an electronic control unit for controlling at least the pump, wherein the electronic control unit comprises a memory and a processor and is adapted to receive at least a first parameter from at least one sensor of the bioreactor cleaning system and at least a second parameter from a user via a human-machine interface, and wherein the electronic control unit controls the pump based on the first and second parameters.

5. The bioreactor cleaning system of claim 1, including an acid dosing unit having at least one acid canister connection for connecting one or more acid canisters and at least one base canister connection for connecting one or more base canisters, and being connectable to the acid tank, the fresh water connection and the pump.

6. The bioreactor cleaning system according to claim 5, wherein liquid can be pumped from the acid tank to the acid dosing unit by means of the pump.

7. The bioreactor cleaning system according to claim 5, wherein liquid can be pumped from the first suction connection to the acid dosing unit by means of the pump.

8. The bioreactor cleaning system according to claim 1, wherein liquid can be pumped from the acid tank to the collection tank by means of the pump.

9. The bioreactor cleaning system according to claim 1, including a high-pressure pump upstream of the flushing connection.

10. The bioreactor cleaning system according to claim 1, including a first valve connecting the first suction connection to a second line via a first line.

11. The bioreactor cleaning system of claim 10, including a second valve connecting the second line to the first pump port.

12. The bioreactor cleaning system according to claim 11, including a third valve connecting the second suction connection to a fourth line via a third line.

13. The bioreactor cleaning system of claim 12, including a fourth valve connecting the fourth line to the second pump port.

14. The bioreactor cleaning system according to claim 13, including a fifth valve connecting the second line to the fourth line.

15. The bioreactor cleaning system according to claim 1, wherein the first pump port is connected to the collection tank via a first collection tank valve.

16. The bioreactor cleaning system according to claim 1, wherein the first pump port is connected to the acid tank via a first acid tank valve.

17. The bioreactor cleaning system according to claim 1, wherein the second pump port is connectable or connected to the collection tank via a second collection tank valve.

18. The bioreactor cleaning system according to claim 1, wherein the second pump port is connectable or connected to the acid tank via a second acid tank valve.

19. The bioreactor cleaning system of claim 5, including a recirculation valve connecting the second pump port to the acid dosing unit.

20. The bioreactor cleaning system of claim 1, including a first measuring valve connecting the second pump port to the measuring unit.

21. The bioreactor cleaning system according to claim 1, including a second measuring valve connecting the measuring unit to a first measuring line.

22. The bioreactor cleaning system of claim 21, including a first fresh water valve connecting the fresh water connection to the first measuring line.

23. The bioreactor cleaning system according to claim 22, including a sixth valve connecting the first measuring line to the fourth line.

24. The bioreactor cleaning system according to claim 23, including a seventh valve connecting the first measuring line to the acid tank and/or collection tank via the second acid tank valve and the second collection tank valve, respectively.

25. The bioreactor cleaning system of claim 4, including a level sensor in the measuring unit for detecting a quantity of liquid received in the measuring unit, wherein the level sensor is connected to and provides a measuring level signal to the electronic control unit.

26. The bioreactor cleaning system of claim 4, including a first pH sensor for sensing a first pH of a fluid supplied to the acid tank, wherein the first pH sensor is connected to and provides a first pH signal to the electronic control unit.

27. The bioreactor cleaning system according to claim 4, wherein the electronic control unit comprises code means which, when executed on the electronic control unit, cause it to perform a cleaning procedure comprising one or more cleaning steps for cleaning and maintaining the bioreactor.

28. A cleaning method comprising one or more cleaning steps for cleaning and maintaining a bioreactor by means of a bioreactor cleaning system according to claim 1, wherein the cleaning method comprises:
    suctioning liquid from the bioreactor via the second suction connection; and
    pumping the extracted liquid into the collection tank.

29. The cleaning method according to claim 28, including:
    reading data from the bioreactor via a data link between the bioreactor and the bioreactor cleaning system.

30. The cleaning method according to claim 28, including:
    filling fresh water into the bioreactor via the second suction connection; and
    waiting a predetermined first time.

31. The cleaning method according to claim 28, including:
    supplying liquid to the flushing port for supplying the liquid to a cleaning nozzle of the bioreactor.

32. The cleaning method according to claim 28, including:
    suctioning liquid from the bioreactor via the first suction connection; and
    pumping the extracted liquid into the collection tank or into an acid tank.

33. The cleaning method according to claim 28, including:
    introducing an aqueous acid solution into the bioreactor via the first suction connection and/or the second suction connection; and
    waiting of a predetermined second time.

34. The cleaning method according to claim 33, including:
    introducing compressed air into the bioreactor via the first suction connection.

35. The cleaning method according to claim 34, including:
    filling an aqueous acid solution into the bioreactor via the second suction connection; and simultaneously:
    suctioning liquid from the bioreactor via the first suction connection.

36. The cleaning method according to claim 28, including:
    measuring a predetermined volume of liquid in the measuring unit;
    feeding the predetermined volume of liquid into the bioreactor via the second suction connection;
    waiting of a predetermined third time;
    suctioning liquid from the bioreactor via the first suction connection;
    supplying the extracted liquid to the measuring unit; and
    measuring the volume of the extracted liquid.

37. The cleaning method according to claim 28, including:
    cleaning a sanitizer of the bioreactor.

38. A computer program product comprising code means which, when executed on an electronic control unit of a bioreactor cleaning system, causes the bioreactor cleaning system to perform a cleaning procedure comprising one or more cleaning steps for cleaning and maintaining the bioreactor according to claim 28.

* * * * *